United States Patent [19]

Andersson

[11] Patent Number: 4,786,283
[45] Date of Patent: Nov. 22, 1988

[54] FIXING DEVICE FOR STOMY BAG

[75] Inventor: Sivert Andersson, Strängnäs, Sweden

[73] Assignee: Futuraprodukter HB, Strängnäs, Sweden

[21] Appl. No.: 83,739

[22] PCT Filed: Nov. 21, 1985

[86] PCT No.: PCT/SE85/00476
§ 371 Date: Apr. 29, 1987
§ 102(e) Date: Apr. 29, 1987

[87] PCT Pub. No.: WO87/03192
PCT Pub. Date: Jun. 4, 1987

[51] Int. Cl.⁴ .................................................. A61F 5/44
[52] U.S. Cl. .................................... 604/328; 604/338
[58] Field of Search ............... 623/11, 12, 14; 128/79; 604/335, 337–345, 277, 328, 337–345

[56] References Cited

U.S. PATENT DOCUMENTS 3,392,722  7/1968  Jorgensen .................. 604/256
4,117,847  10/1978  Clayton ..................... 604/328

FOREIGN PATENT DOCUMENTS 802823  9/1936  France .................... 604/338
401974  6/1978  Sweden ................... 604/328

Primary Examiner—Stephen C. Pellegrino
Assistant Examiner—J. L. Kruter
Attorney, Agent, or Firm—Cushman, Darby & Cushman

[57] ABSTRACT

At a fixing device for a stomy bag a counter-holding ring (2) is intended to be operated under a patient's outer skin (3) when the intestine (4) is sewed on. A tubular body (1), one end of which is provided with a flange (5) and to which the stomy bag (18) is intended to be connected and whose outer diameter will permit the body (1) to be moved through the counter-holding ring (2) with the flange (5) until contact with the outer skin (3), is provided with an outer peripheral portion (6) of an elastically ductile material and an annular cavity (7) arranged inside this and associated with the outside of the body (1) via a first channel (8).

4 Claims, 2 Drawing Sheets

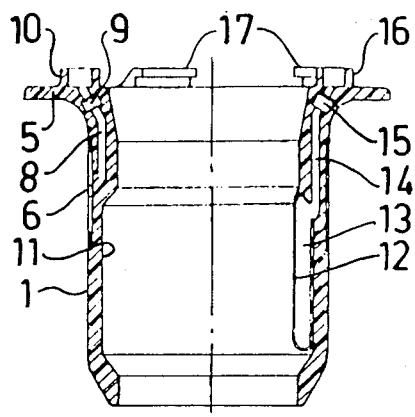
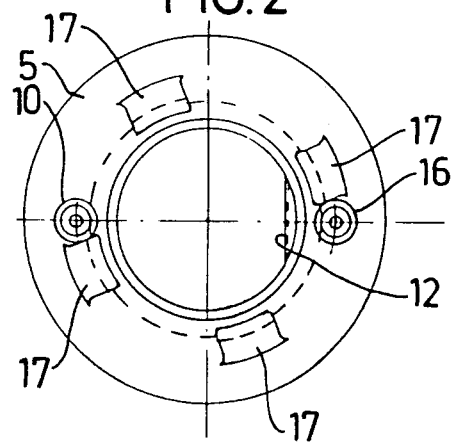
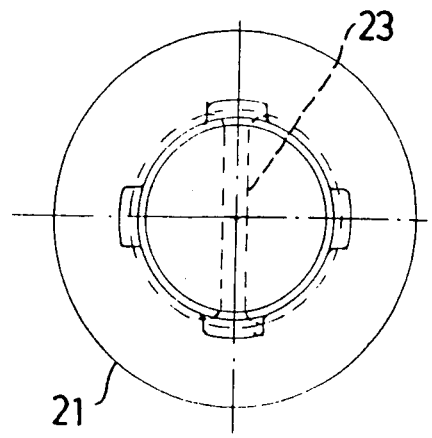
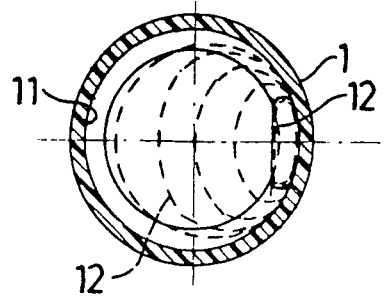
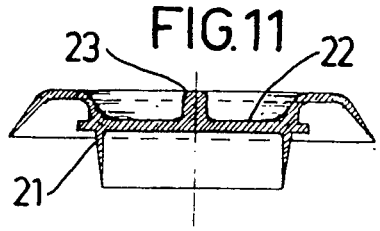

FIXING DEVICE FOR STOMY BAG

BACKGROUND OF THE INVENTION

This invention relates to a fixing device for a stomy bag (enterostomy) intended to improve the situation for stomy-operated persons.

The fixing means for stomy bags found on the market have great disadvantages. Thus, fixing devices or attaching plates for stomy bags are used, which plates must be attached to the skin by means of adhesive ties. Moreover, self-adhering bags without an attaching plate occur as well as plates attached to belts which must also be sealed against the carrier's skin by means of adhesive ties. These means of attachment have such after-effects that wounds arise on the skin caused by allergy or mechanical irritation. Leakage of intestinal contents will often occur and become a nuisance to the patient.

As a rule, the connection between the stomy bag and the attaching plate or attaching means is so embodied that a great force is needed for the connection of the bag to the attaching means in order to obtain the best possible sealing. Further, the commonly used sealing groove of the connection must be carefully cleaned to obtain the best possible sealing at the time of exchange of bags. There has been no possibility of sealing the intenstinal orifice at removed stomy bag.

SUMMARY OF THE INVENTION

It is the object of this invention to eliminate the above-mentioned disadvantages by providing, in combination, the features of the invention defined in the appended claims.

BRIEF DESCRIPTION OF THE DRAWINGS

The invention will be described in greater detail in the form of an example with reference to the drawings, in which FIG. 1 is a lateral section of an embodiment of the invention, FIG. 2 is a top plan view of the device according to FIG. 1.

FIG. 6 is a schematic cross-section of the function of the cut-off device, FIG. 10 is a top plan view and FIG. 11 a lateral view of a cover which can be applied to the device instead of the stomy bag.

DETAILED DESCRIPTION

In principle, the fixing device of the invention can be said to consist of two parts, namely a substantially tubular body 1 and a counter-holding ring 2.

Figure 3:
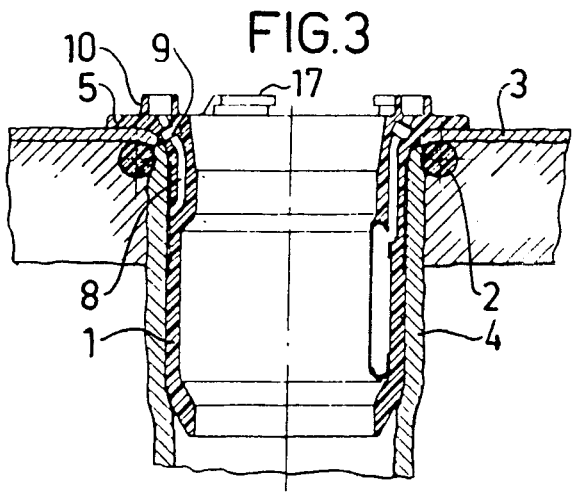
FIG. 3 is a section of the device according to the invention shown in FIGS. 1 and 2 and inserted in the intestinal orifice.
Figure 4:
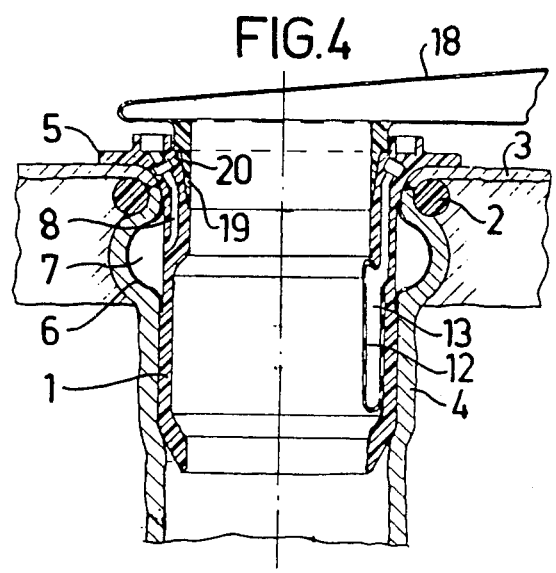
FIG. 4 is a section of the device fixed in the intestinal orifice and with an applied stomy bag (only a part thereof is shown).
Figure 5:
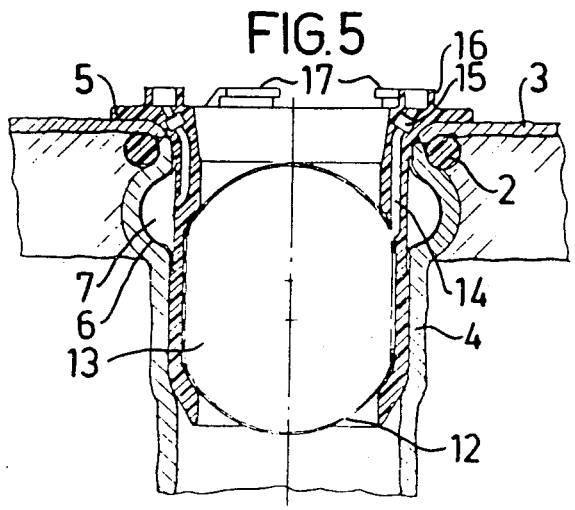
FIG. 5 is a section of the device secured in position in the intestinal orifice and with activated cut-off valve.

The counter-holding ring 2 shown in FIGS. 3–5 can, for instance, consist of a plastic or similar material. The ring 2 is operated under the carrier's outer skin 33 when the intestine 4 is sewn onto the outer skin.

The tubular body 1 has a diameter permitting insertion of the body through the counter-holding ring to a position shown in FIG. 3 where a flange 5 of the body 1 will get in contact with the outer skin 3. As is apparent from the figures, the intestine 4 will be placed around the inwardly, directed tubular body 1 which, therefore, has well-rounded edges, like, of course, the counter-holding ring 2. The tubular body 1 is provided with an outer peripheral portion 6 of an elastically ductile material with an annular cavity 7 lying inside thereof. This cavity is, via a channel 8 and a nonreturn valve 9, associated with the outside of the flange 5, where the channel 8 ends in a socket-like opening 10.

The channel in the tubular body 1 has an enlarged diameter along a portion 11. On one side of the channel wall and along said portion 11 a gas-tight bladder 12 is arranged, the interior 13 of which is associated with a socket-like opening 16 on the outside of the flange 5 via a channel 14 and a nonreturn valve 15.

When the fixing device or the tubular body 1 has been positioned with the flange 5 in contact with the carrier's skin, as is apparent from FIG. 3, the annular cavity 7 is set under pressure, whereby the peripheral portion 6, which will be inside the counter-holding ring 2 in this position, will extend fixing the body 1 in position in the intestine 4. The pressure in the annular cavity 7 is, for instance, brought about by blowing air through the channel 8 by means of a pump, the nozzle of which is applied to the socket-like opening 10. The non-return valve 9 prevents the blown air from leaving the cavity 7. It is also possible, instead of using a pump, to blow directly in a hose, the free end of which is applied to the socket 10.

In this mounted state, the intestine 4 is clamped to the counter-holding ring 2, a good sealing and fixing of the body 1 thus being obtained.

The flange 5 has on its outside a bayonet catch in the form of four lugs 17. Of course, the bayonet catch can be formed in several different manners within the scope of the knowledge of one skilled in the art, the details of which are not part of the invention.

FIG. 4 shows the body 1 fixed in the intestinal orifice in the way described above, with a stomy bag 18 adapted via the bayonet catch 17. Only part of the stomy bag is shown. Besides the parts corresponding to the bayonet catch 17, the stomy bag 18 has a tapered connection 19 with a sealing shoulder 20, the tapered connection being intended to be received in a corresponding tapered part of the mouth of the channel of the body 1. The connection and the shoulder are of a coarser material than the stomy bag, but can of course be formed of the same material and integrally with the stomy bag.

Thus, as will be understood, FIG. 4 shows a section of the whole fixing device with mounted stomy bag adapted to the carrier's body and ready for use.

In case it is desirable to seal the intestinal orifice, i.e. to seal the channel of the tubular body 1, air is, for intance, introduced under pressure via the nozzle 16, the nonreturn valve 15 and the channel 14 to the interior 13 of the bladder 12. When enough air has been itroduced into the interior of the bladder, the bladder 12 will quite stop-up the channel of the tubular body 1, which is shown in FIG. 5. By forming the portion 11 with an enlarged diameter, a good guiding and sealing contact of the bladder to the whole peripheral inside of the channel is obtained. In FIG. 6 the phases of the expansion of the bladder 12 at inflation are shown with dashed lines. The nonreturn valve 15 prevents the air in the bladder from streaming out. A reliable sealing of the intestinal channel has now been achieved. The bladder 12 can be inflated and deflated in the same way and by the same means as applies to the portion 6.

It is now possible, instead of the stomy bag 18, to apply a cover 21 on the bayonet catch 17 of the tubular body 1, as shown in FIGS. 10 and 11. The connection of the cover to the opening of the body 1 corresponds to the connection of the stomy bag and the cover is provided with a grip 23 arranged in a recess 22. The recess 22 can be filled with a soft material permitting access to the grip 23 and the cover can be skin-colored. The carrier of the device according to the invention is, by means of the device, given a possibility of associating with other persons in a freer and easier fashion, e.g. bathing, without being troubled with a stomy bag.

Figure 7:
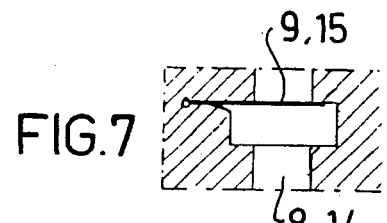
FIGS. 7, 8 and 9 show schematically the function of a valve included in the device.
Figure 8:
Figure 9:
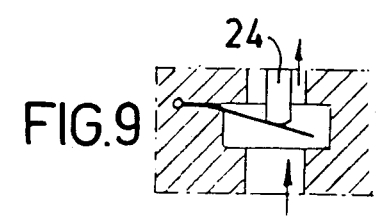

FIGS. 7-9 show schematically the function of the nonreturn valves 9 and 15. The nonreturn valves are indicated in the figures in the form of simple membrane valves and the valve can be easily opened for release of air in the space 7 or 13 by the aid of a thin rod 24 or the like which is applied to the spring tongue.

Thus, the tubular body 1 is formed with a certain thickness and stiffness while the outer peripheral portion 6 as well as the bladder 12 are made of a thin, ductile material.

It will be understood that it is possible within the scope of the invention to embody the different parts described above in other ways than those shown here and several bladders, for example three, can for instance be used evenly distributed along the inner periphery of the portion 11 instead of one single bladder 12. Of course, the fixing device can be designed with merely the locking means, i.e. the inflatable peripheral portion 6, engaging inside the ring 2, and the cut-off device 12 being omitted.

I claim:

1. A device for fixing a stomy bag to a person having an intestine end opening through an artificial opening provided in the person's outer skin at a site where the intestine end is sewn perimetrically about the opening, to the person's outer skin, said device comprising:

a tubular body having an inner end and an outer end, an outer peripheral sidewall and an inner peripheral sidewall; a radially outwardly extending annular flange provided externally on said tubular body adjacent said outer end, whereby said tubular body may be axially inserted within the intestine, inner end first, into said intestine end through said artificial opening, until said flange abuts said outer skin;

a counter-holding ring adapted to be received in circumferentially surrounding relation to said intestine end beneath the person's outer skin, so that as the inner end of the tubular body is telescoped into the intestine end through said artificial opening, the intestine end becomes radially trapped between the outer peripheral sidewall of the tubular body and the counter-holding ring, and the person's outer skin becomes axially trapped between said annular flange and the counter-holding ring;

means providing an externally-bulgeable, flexible-walled annular cavity means on said outer peripheral sidewall of said tubular body at an axially intermediate location near said outer end, whereby, after said counter-holding ring and said tubular body have been installed in relation to the person's intestine end and outer skin, said cavity means may be inflated and thereby externally bulged for radially outwardly distending a portion of the persons' intestine and axially behind the counter-holding ring for locking the tubular body in place against axially outward detelescoping movement;

one-way valved channel means opening outwardly through said annular flange at a socket and communicating axially and radially through said tubular body with said cavity means for permitting deflatable inflation of said cavity means; and lug means provided on said annular flange so that an externally-worn stomy bag may be removably mounted to the outer end of the tubular body.

2. The stomy bag fixing device of claim 1, further including:

means providing at least one internally-bulgeable, flexible-walled bladder on said inner peripheral sidewall of said tubular body at an axially intermediate location, whereby, after said counter-holding ring and said tubular body have been installed in relation to the person's intestine and outer skin, and said cavity means has been inflated to lock the tubular body in place, the at least one bladder can be deflatably inflated for openably closing-off said intestine end at said tubular body; and a second one-way valved channel means opening outwardly through said annular flange at a second socket and communicating axially and radially through said tubular body with said at least one bladder for permitting deflatable inflation of said at least one bladder.

3. The stomy bag fixing device of claim 2, further including:

a stomy bag having an end fitting removably mounted to said annular flange by said lug means.

4. The stomy bag fixing device of claim 2, further including:

a handgrip-provided cover for removable mounting to said annular flange by said lug means in lieu of a stomy bag, for removably closing said outer end of said tubular body from externally of the person's outer skin.

* * * * *